US011950646B2

(12) United States Patent
Forzani et al.

(10) Patent No.: US 11,950,646 B2
(45) Date of Patent: Apr. 9, 2024

(54) HAND WARMER

(71) Applicant: Galvani Tech Apparel Inc., Calgary (CA)

(72) Inventors: John Forzani, Bellevue, WA (US); Jesse Galvon, Calgary (CA)

(73) Assignee: Galvani Tech Apparel Inc., Calgary (CA)

( * ) Notice: Subject to any disclaimer, the term of this patent is extended or adjusted under 35 U.S.C. 154(b) by 0 days.

(21) Appl. No.: 15/777,293

(22) PCT Filed: Nov. 21, 2016

(86) PCT No.: PCT/CA2016/000287
§ 371 (c)(1),
(2) Date: May 18, 2018

(87) PCT Pub. No.: WO2017/083958
PCT Pub. Date: May 26, 2017

(65) Prior Publication Data
US 2018/0333294 A1    Nov. 22, 2018

(30) Foreign Application Priority Data

Nov. 20, 2015  (CA) ................................ CA 2912509
Aug. 15, 2016  (CA) ................................ CA 2939303

(51) Int. Cl.
*A61F 7/00*    (2006.01)
*A41D 13/08*   (2006.01)
(Continued)

(52) U.S. Cl.
CPC .............. *A41D 13/081* (2013.01); *A61F 7/00* (2013.01); *A61F 7/007* (2013.01); *H05B 3/36* (2013.01);
(Continued)

(58) Field of Classification Search
CPC .............. A61F 7/007; A61F 2007/0071; A61F 2007/0078; A61F 2007/0087;
(Continued)

(56) References Cited

U.S. PATENT DOCUMENTS 3,644,705 A * 2/1972 Johnson ................. H05B 3/342
                                                   219/211
4,221,954 A * 9/1980 Cohen ..................... A61F 7/007
                                                      2/66
(Continued)

FOREIGN PATENT DOCUMENTS

CA         2544906        10/2006
CA         2842113         8/2015
(Continued)

OTHER PUBLICATIONS

International Search Report prepared by the Canadian Intellectual Property Office dated Feb. 15, 2017, for International Application No. PCT/CA2016/000287.

*Primary Examiner* — Justin C Dodson
(74) *Attorney, Agent, or Firm* — Ellenoff Grossman & Schole LLP; John C. Stellabotte; Danielle Cohen

(57) ABSTRACT

A hand warmer comprising: a tubular sleeve having two extremities located along a longitudinal axis thereof, said sleeve defining a longitudinal opening therein, each extremity having defining an opening adapted to receive hands; a heating element; and a battery operatively connected to the heating element; wherein said tubular sleeve comprising an inner wall and an outer wall and adapted to receive the battery between the inner and outer wall and wherein the heating element is located within the longitudinal opening and is adapted to be grasped by a hand when such is inserted into the longitudinal opening of the hand warmer.

9 Claims, 5 Drawing Sheets

(51) Int. Cl.
*H05B 3/36* (2006.01)
*A41D 1/04* (2006.01)
*A61F 7/02* (2006.01)
*H02J 7/00* (2006.01)

(52) U.S. Cl.
CPC ............ *A41D 1/04* (2013.01); *A41D 2400/12* (2013.01); *A61F 2007/0036* (2013.01); *A61F 2007/0072* (2013.01); *A61F 2007/0078* (2013.01); *A61F 2007/0087* (2013.01); *A61F 2007/0095* (2013.01); *A61F 2007/0096* (2013.01); *A61F 2007/0233* (2013.01); *A61F 2007/0238* (2013.01); *H02J 7/0013* (2013.01); *H02J 7/0042* (2013.01); *H02J 7/0048* (2020.01)

(58) Field of Classification Search
CPC ...... A61F 2007/0095; A61F 2007/0088; A61F 2007/0228; A61F 2007/0295; A61F 2007/0029; A61F 2007/0035; A61F 2007/0036; A61F 2007/0233; A61F 2007/0226; A61F 2007/0001; A61F 2007/0225; A61F 2007/0231; A61F 2007/0032; A61F 2007/0034; A61F 2007/0223; A61F 2007/023; A61F 2007/0246; A61F 2007/0249; A61F 2007/0082; A61F 13/108; A61F 2013/00187; A61F 2013/00195; A61F 2013/002; A61F 5/0109; A61F 5/0118; H05B 1/0272; H05B 3/347; H05B 3/145; H05B 3/146; H05B 3/342; H05B 3/0071; H05B 3/34; H05B 3/42; H05B 2203/011; H05B 2203/033; H05B 2203/036; H05B 2203/032; H01M 2220/30; H01M 10/425; H01M 2/1022; H05K 5/0017; H05K 5/0213; B29L 2031/779; F28D 2021/005
USPC ....... 219/211, 494, 201, 529, 209, 506, 527, 219/200, 240, 481, 483, 520, 539; 2/160, 2/102, 69, 169, 161.1, 167, 243.1, 247, 2/458; 174/74 R, 102 R, 108, 110 R, 174/254; 248/314; 252/502, 510
See application file for complete search history.

(56) References Cited

U.S. PATENT DOCUMENTS

| | | | |
|---|---|---|---|
| 4,862,519 A | 9/1989 | Bull | |
| 5,139,187 A | 8/1992 | Fowler | |
| 5,499,401 A | 3/1996 | Heinmiller | |
| 6,060,693 A * | 5/2000 | Brown | A41D 19/01535 2/163 |
| 7,496,969 B2 * | 3/2009 | Pieczynski | A45C 3/14 2/16 |
| 8,217,318 B1 * | 7/2012 | Wood-Putnam | B63C 11/02 219/211 |
| 8,946,598 B2 * | 2/2015 | Hasegawa | H05B 3/34 219/548 |
| 2002/0153368 A1 * | 10/2002 | Gardner | B29C 70/885 219/545 |
| 2006/0248624 A1 * | 11/2006 | Pieczynski | A41D 13/081 2/16 |
| 2009/0032520 A1 * | 2/2009 | Cronn | H05B 3/565 219/211 |
| 2010/0175161 A1 * | 7/2010 | Jarboe | A41D 13/085 2/69 |
| 2012/0273479 A1 * | 11/2012 | Kim | H05B 3/342 219/494 |
| 2015/0226497 A1 * | 8/2015 | Wang | F28D 15/0233 165/104.28 |
| 2015/0312965 A1 * | 10/2015 | Chen | A41D 13/0051 219/211 |
| 2017/0013677 A1 * | 1/2017 | Chen | H05B 3/06 |

FOREIGN PATENT DOCUMENTS

| | | | |
|---|---|---|---|
| CN | 103222912 A * | 7/2013 | ........... A41D 13/081 |
| GB | 2136674 | 9/1984 | |
| KR | 10-2013-0095942 | 8/2013 | |

* cited by examiner

HAND WARMER

CROSS REFERENCE TO RELATED APPLICATIONS

This application is a national stage application under 35 U.S.C. 371 and claims the benefit of PCT Application No. PCT/CA2016/000287 having an international filing date of 21 Nov. 2016, which designated the United States, which PCT application claimed the benefit of Canada Patent Application No. 2,912,509 filed 20 Nov. 2015, and Canada Patent Application No. 2,939,303 filed 15 Aug. 2016, the disclosure of each of which are incorporated herein by reference.

FIELD OF THE INVENTION

The present invention is directed to a hand warmer, more specifically a hand warmer comprising a novel heating element that can be grasped by a user's hands.

BACKGROUND OF THE INVENTION

CN203506961 teaches a hand warmer pocket, and particularly relates to a novel temperature-adjustable liquid-free hand warmer pocket. The novel temperature-adjustable liquid-free hand warmer pocket is mainly composed of an outer cover, a guide wire and a thermal sensing switch. The hand warmer pocket further comprises an electric heating piece and a cotton fiber bag. The electric heating piece is electrically connected with the thermal sensing switch, and the thermal sensing switch is electrically connected with the guide wire. The electric heating piece wraps the outside of the cotton fiber bag, and the cotton fiber bag and the electric heating piece are arranged in the woolen outer cover. According to the novel temperature-adjustable liquid-free hand warmer pocket, safety voltages are used for working, the varieties of power supplies are wide, safety is achieved, explosion hazards are avoided, temperatures can rise quickly, the heating temperature is stable, carrying is convenient, and the novel temperature-adjusting liquid-free hand warmer pocket can be effectively used outdoors for a long time, and the using temperature can be adjusted.

U.S. Pat. No. 8,615,814 (B1) teaches a hand muff having a main body which includes a generally cylindrical member having an opening at each opposite end thereof. A viewing panel forms a section of a generally cylindrical wall of the main body of the hand muff. The viewing panel can be formed of one or both of solid transparent material and screen mesh material. A selectively removable cover flap permits the user to see inside the muff when the free edge of the cover flap is selectively detached from the body of the muff. A pocket with a closure is provided inside the body of the muff and is configured to hold a cell phone, a personal digital assistant and the like handheld device KR20130095942 discloses a hand stove using a battery includes a power supply part (10) including a lithium ion battery; a heating part (20) for generating heat by supplying power from the power supply part; a charging state display part (30) displaying the charged state of the battery; a control switch part (40) for turning on and off the power supply from the power supply part; and a housing part for accommodating the components.

U.S. Pat. No. 5,139,187 (A) teaches a body garment having utility as a hand warmer, fanny pack or carrier of elongated articles such as skis. The garment includes a centrally located, tubular, synthetic fleece member of relatively long axial length having a hand warmer chamber with a synthetic moisture wicking cloth lining. A first zipper in the top of the tubular member provides access to the hand warmer chamber and to an open-mesh heat source bag that is located within the hand warmer chamber. A pair fleece cuffs are stitched with on each open end of the tubular member. A pair of cords is attached to each cuff to compliantly control the size of the cuff open ends.

U.S. Pat. No. 4,862,519 (A) teaches a fanny pack in combination with an insulated hand warmer muff provides a device for carrying objects and a hand warming device, each of which can be used independently of the other. The hand warmer pack is worn to the rear of the user's body on the hips. When turned to the front of the user's body the user's hands may be inserted into an insulated hand warmer muff through separate openings which do not give access to the compartment in which objects are carried. With the muff removed, the other contents of the pack are unaffected, while the muff can still be used to warm the hands, or opened flat as a seat cushion. The pocket which housed the muff is then available for additional carrying space, while the contents of the main compartment or fanny pack are accessible by means of a separate opening at the top.

CN2158700 discloses provides a heat-insulating cover for an electric hand warmer, which is characterized in that pile fabrics are used for manufacture a cover, wherein the cover forms an animal shape or in a cylindrical structure. The inner layer of the cover is provided with an inner bag, and an electric hand warmer can be put in the inner bag. An opening of the inner bag is sewed and connected with an opening of the lower side (or the upper side) of the cover. The electric hand warmer can be put in the inner bag through the opening at the lower side (or the upper side) of the cover, and an opening of the inner bag is provided with a zipper. The utility model has the advantages of beautiful appearance and good heat-insulating effect.

CN203915207 discloses a hand warmer bag which comprises a sealing bag, wherein the sealing bag is filled with heating liquid; the heating liquid is heated by an electrical heating device; the hand warmer bag further comprises an alarming protective device; the alarming protective device comprises a protective bag arranged outside the sealing bag in a sleeving manner, a humidity sensor arranged between the protective bag and the sealing bag and a warmer electrically connected with the humidity sensor; the humidity sensor and the warmer are powered by a power supply to work normally. It is stated that through the adoption of the hand warmer bag with the structure, the humidity between the protective bag and the sealing bag can be detected by the humidity sensor, higher humidity indicates the breakage and water leakage of the protective bag, the humidity sensor can feed the signal back to the warmer, the warmer gives an alarm to a user and burning and other potential safety hazards caused by the water leakage to the user can be effectively avoided.

Despite the prior art listed above, there still exists a need for a more efficient hand warmer capable of heating and retaining heat more efficiently and lasting longer than known devices all the while being portable in such a fashion as to be carried out on the field during sports play, such as football, golf, etc.

SUMMARY OF THE INVENTION

According to one aspect of the present invention, there is provided a hand warmer comprising a heating element which is located within an internal space defined by a tubular sleeve.

According to a preferred embodiment of the present invention, the hand warmer further comprises at least one heating element located within the space defined by the interior wall of the tubular sleeve and the exterior wall of the tubular sleeve.

According to a preferred embodiment of the present invention, the heating element located within an internal space defined by a tubular sleeve is in the shape of a handlebar and can be grasped by a hand and provide direct heat to said hand as opposed to heating material surrounding said hand. Preferably, the handlebar substantially extends from one opening of the sleeve to the opposite opening. Preferably also the heating element is secured to the interior of the tubular sleeve at both ends and proximate to the openings in the sleeve. More preferably, the heating element is secured at a bottom portion of the internal wall of the sleeve. According to a preferred embodiment of the present invention, the handlebar heating element is parallel to the longitudinal opening of the sleeve so as to allow hands to grasp such as if it were handlebars of a bicycle, for example. According to another preferred embodiment of the present invention, the handlebar heating element is perpendicular to the longitudinal opening of the sleeve so as to allow hands to grasp such as if it were a bottle or similar vertical object.

According to another aspect of the present invention, there is provided a hand warmer comprising a heating element located within an internal space defined by a tubular sleeve and a substantially self-closing fabric located around each opening of the tubular sleeve. Said substantially self-closing fabric is to be understood in this instance as a fabric which, when pressed together, forms a closure which requires a mild to moderate mechanical force to peel apart. This closing feature allows to retain the heat generated within the sleeve of the hand warmer when hands are removed therefrom. This substantially self-closing fabric can be selected form the group consisting of VELCRO® and similar type fabrics such as those which comprises oppositely ionic charged layers which, when pressed against one another result in the oppositely charged layers to be closed together.

For the spacer used as the inner tube against the skin, one should note that spacer knits are double-layered circular knits with a cushion of air and spring-like yarns between the two sides. This unique fabric class is knit in one continuous operation. Although it looks like several fabrics bonded together, it is actually one fabric that cannot be separated by layer. Special yarns are selected for aesthetic qualities (i.e. soft hand, bright/dull, etc.) and for performance properties (i.e. moisture transport, thermal insulation or conductance, anti-microbial, etc.).

According to a preferred embodiment of the present invention, the hand warmer will further comprise at least one heating element located within the space defined by the internal wall and the external wall of the sleeve. In a preferred embodiment, the hand warmer will comprise a heating element located in a front portion of the hand warmer and a heating element located in a back portion of the hand warmer. For clarification, the front portion of the hand warmer is understood to be the portion situated away from the body of the user when it is located proximate the user's mid-section. The back portion of the hand warmer is thus understood to be the portion of the hand warmer situated proximate to the user's mid-section.

According to a preferred embodiment of the present invention, the hand warmer will further comprise a battery operatively connected to three heating elements. Preferably, the battery is a lithium battery and can be recharged prior to use.

According to a preferred embodiment of the present invention, the hand warmer will further comprise at least one means for securing the hand warmer around the waist of a user. Such means for securing the hand warmer around the waist of a user includes toggle clips, VELCRO®, press studs, drawstring, slide release buckle, etc. Most preferred is the slide release buckle.

According to another aspect of the present invention, there is provided a hand warmer comprising a heating element which is located within an internal longitudinal space defined by the inside of a tubular sleeve; substantially self-closing fabric located around the openings in the tubular sleeve; and a heat capture fabric substantially surrounding the entire sleeve and located within the space defined by the internal and external walls of the sleeve. Preferably, the hand warmer comprises a water repellent fabric on the outer surface thereof to reduce the possibility of the walls of hand warmer from getting wet.

According to a preferred embodiment of the present invention, the sleeve of the hand warmer will have a downward arcuate shape to facilitate the insertion of hands therein.

According to a preferred embodiment of the present invention, the heating elements are actuated through a switch or button preferably located on external surface of sleeve. In a more preferred embodiment, the heating elements can provide various levels of heat or a range of heat. According to an even more preferred embodiment of the present invention, the actuator further comprises a visual indicator showing the heat level setting of the hand warmer.

According to another aspect of the present invention, there is provided a hand warmer capable of providing extended battery efficiency through the use of heat capture fabric, substantially self sealing fabrics, a heating element not located within the space defined by the interior and exterior walls of the sleeve.

BRIEF DESCRIPTION OF THE FIGURES

The present invention may be better understood in consideration of the following description of various embodiments of the invention in connection with the accompanying figures, in which.

DETAILED DESCRIPTION OF A PREFERRED EMBODIMENT OF THE INVENTION

The hand warmer according to the present invention provides for improved hand warming and battery efficiency through the novel application of an internal heating element which can be grasped by a user's hands and hence accelerate the warming of the user's hands.

An adjustable length belt allows the hand warmer to be attached around the waist of a user. The belt is secured to the sleeve either by stitching or through slide release buckles or the like.

Figure 1:
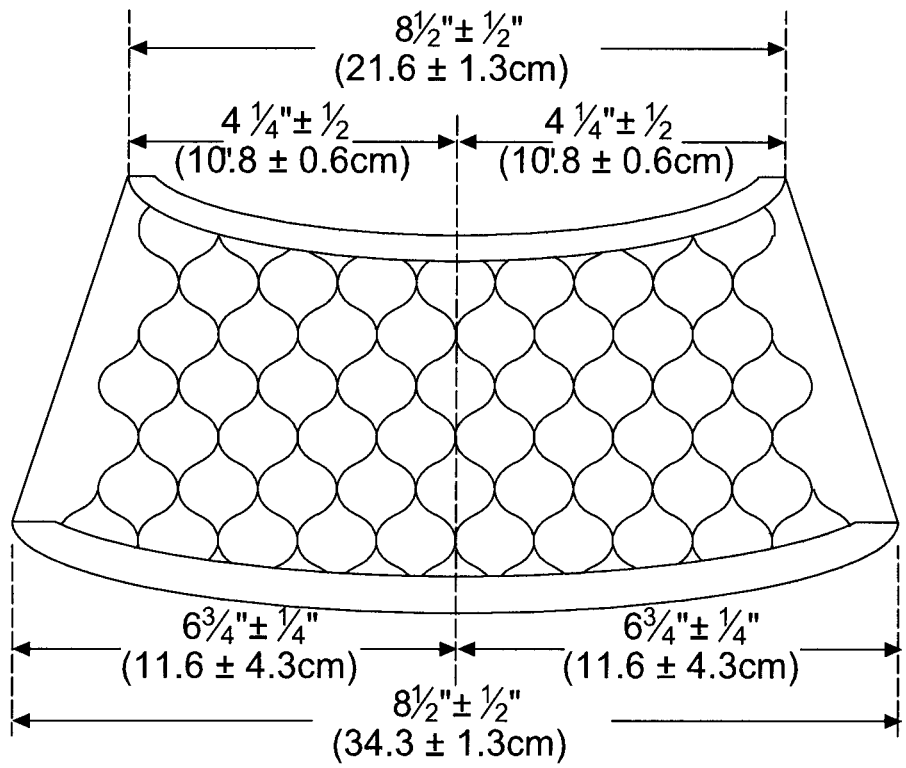
FIG. 1 is a schematic view of an outer heating element pad showing length dimensions of the hand warmer according to a preferred embodiment of the present invention.

FIG. 1 is a front view of the heating pad of the hand warmer according to a preferred embodiment of the present invention. This figure illustrates the downward arcuate shape of the hand warmer. The hand warmer according to the preferred embodiment is thus adapted for easy insertion of the hands therein.

At either end of the hand warmer are located the openings (not shown). Each opening has a diameter sized for easy hand insertion but not overly large as to create a potential large heat loss. The space defined by the internal and external walls of tubular sleeve of the hand warmer are preferably filled with down in order to maintain the heat generated by the heating elements. Alternatively, the down could be replaced by a material such as fleece or the like. Alternatively, a synthetic fleece material can be used. Preferably, a moisture wicking lining can be used on the inside portion of the hand warmer sleeve.

In the preferred embodiment illustrated in FIGS. 1 through 4, the hand warmer comprises three heating elements: the heating element positioned in the front section of the tubular sleeve, the heating element positioned in the back section of the tubular sleeve, and the heating element positioned within the opening in the sleeve where the hands are to be inserted for warming.

According to the illustrated embodiment, the third heating element is adapted to be secured to the sleeve in such a way as to free up substantially the entire length of the heating element. Thus, in the embodiment illustrated, the heating element is secured at both ends thereof to a point proximate each opening of the sleeve. Preferably, the point of attachment is at a lower section of the inside of the sleeve so as to minimize encumbrances when inserting one's hands into the hand warmer. In another embodiment, the third heating element may be shorter than the longitudinal internal space within the sleeve and thus may not necessarily span the length of the sleeve, in which case, the points of attachment of the heating element would be somewhat removed from the openings in the sleeve. In a preferred embodiment, it is desirable to have as few points of attachment as possible and it is also desirable that these be as compact as possible to allow more room on the heating element to be grasped by the user's hands.

The sleeve is covered at or proximate the external walls thereof with a heat capturing fabric adapted to retain as much as possible the heat generated by the hand warmer and maintain the desired temperature using as little as possible the heating elements and consequently extending the battery life. Fabrics which may be used for the sleeve also include synthetic moisture wicking fabric such as Polartek® single faced velour material. Polartek® is a hollow core polyester material having good moisture wicking and heat insulating properties.

The sleeve may be covered by fabric reflecting a team's logo, company logo, etc., this may be done by adding a removable fabric (with a zipper for example) or by stitching the fabric onto the hand warmer.

Electrical/Heating Features of the Product

The hand warmer according to a preferred embodiment of the present invention is engineered to ergonomically deliver heat to a user's hands. The heated handle allows to deliver immediate heat to a user's hand. The heating elements are powered by a rechargeable 11.1V Lithium Ion battery. The design of the hand warmer allows to easily replace batteries for extended lifetime. The device is equipped with mart electronics control which provides 4 heat settings. The device is further equipped with an AC Wall charger. The lightweight design allows for dynamic motion and use during game play. There is built-in a temperature microprocessor controller technology. The use wearing the hand warmer will not feel the heating wire. By grabbing the handle, the user heats the palms of his hands while the heating pads incorporated within the walls of the sleeve heat the outside of the user's hands. An adjustable buckle strap will securely hold the hand warmer around a user's waist. The metallic heating fibers allow for an even distribution of heat throughout the hand warmer. The special fabric blends allows for noise reduction which is a substantial advantage for hunters. The flexible heating elements allow maximum mobility with minimal invasiveness. The device preferably further comprises a concealed battery compartment for quick and easy battery replacement closed by zipper.

Heating System

By attaching these pads to a power source, they will generate heat in the hand warmer. In a preferred embodiment of the invention, each hand warmer will use two of the larger curved pads and one smaller, straight pad. It is made of cotton mixed fabric with a flexible metal wire inside used as a heating coil. The heating wire is preferably made of Nickel-chromium (nichrome) wire.

Outer Portion of the Hand Warmer Heating Element Design Requirements

Figure 2:
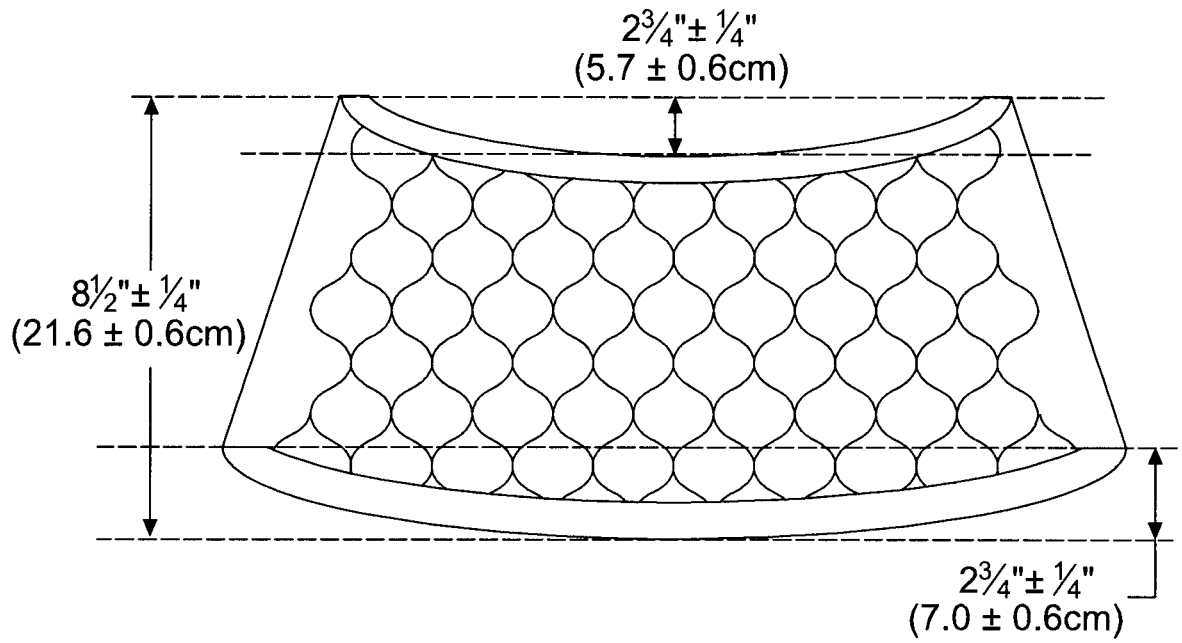
FIG. 2 is a schematic view of an outer heating element pad showing height dimensions of the hand warmer according to a preferred embodiment of the present invention.

According to a preferred embodiment, the outer heating pad elements will have the characteristics described below and as illustrated in FIGS. 1 and 2. Preferably, the heating pad required should have the curved shape depicted in FIGS. 1 and 2.

This heating pad is preferably very thin and flexible. It is manufactured using either one or two layers of thin material. The material used must preferably be able to withstand elevated temperature.

Preferably, the pad of the hand warmer must be made of materials able to withstand elevated temperatures of up to 120 degrees Celsius. Some of the characteristics of a preferred embodiment of the pad outer heating elements used in the hand warmer are shown below in Table 1.

TABLE 1

Characteristics of the pad for the outer heating elements present in the hand warmer

Figure 3:
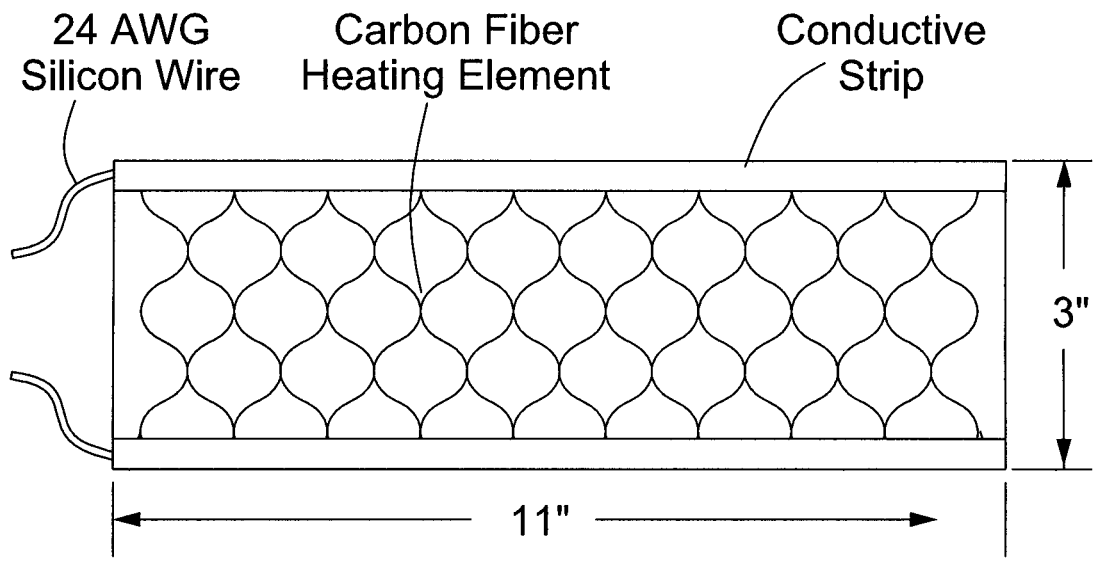
FIG. 3 is a schematic view of the handle heating element pad showing length and height dimensions of the hand warmer according to a preferred embodiment of the present invention.
Figure 4:
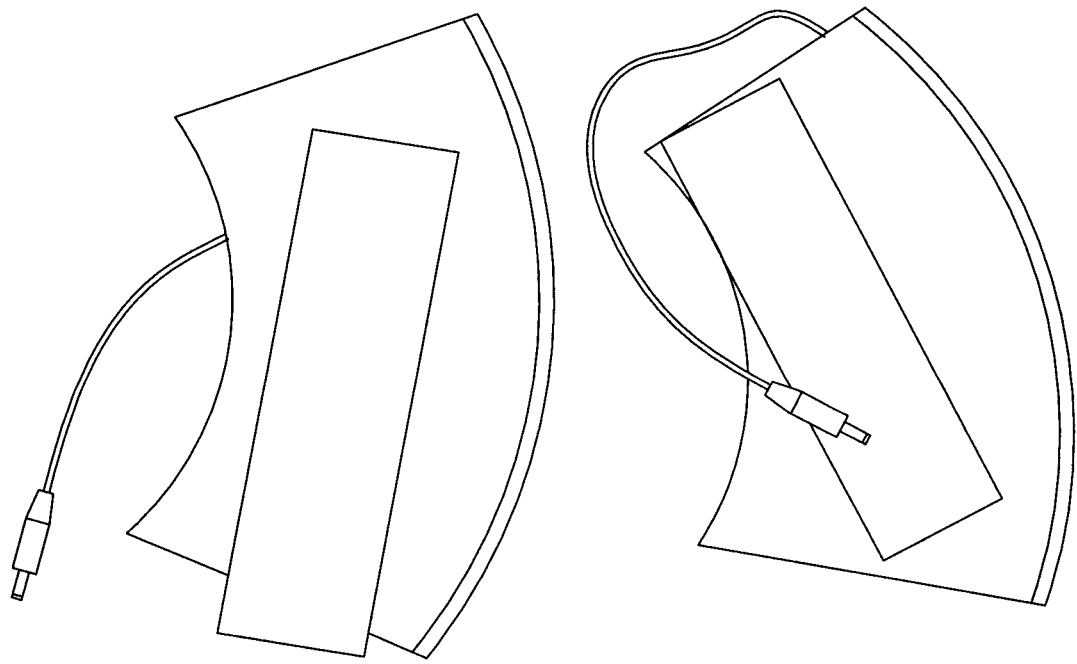
FIG. 4 is a front view of two outer heating elements along with connecting wires of the hand warmer according to a preferred embodiment of the present invention.

| | |
|---|---|
| Length | As shown in FIG. 3 |
| Height | As shown in FIG. 4 |
| Thickness | 2 mm maximum |
| Total Resistance | 3.9 Ω with a tolerance of +0.2 Ω or −0.4 Ω |
| Connecting Wires | 24 AWG Silicon |
| Power Characteristics | Withstand 6.8 V at 1.75 A (12 Watts) |

TABLE 1-continued

Characteristics of the pad for the outer heating elements present in the hand warmer

| | |
|---|---|
| Maximum Operating Temperature | 120° C. |

Heating Handle Element (Inner Pad)

According to the preferred embodiment illustrated, the inner heating pad will be a close replica of the outer heating pad elements but with differences in dimensions and resistance. The heating handle element has the characteristics described below in Table 2 and shown in FIG. 3. This heating pad must be very thin and flexible. Some of the characteristics of a preferred embodiment of the pad used in the hand warmer are shown below in Table 2.

TABLE 2

Characteristics of the heating pad for the handle element present in the hand warmer

| | |
|---|---|
| Total Length | 11" (27.9 cm) |
| Total Height | 3" (7.6 cm) |
| Thickness | 2 mm maximum |
| Total Resistance | 1.22 Ω with a tolerance of +0.10 Ω or −0.10 Ω |
| Connecting Wires | 24 AWG Silicon |
| Power Characteristics | Withstand 4.3 V at 3.5 A (15 Watts) |
| Maximum Operating Temperature | 120° C. |

Preferably, the pad heating element should be very flexible; there should preferably be no aluminum, reflective material on this pad. Preferably also, only one layer of material should be used to secure the carbon fiber heating element. If two layers must be used, ideally one should use the thinnest material that can withstand the specified elevated temperatures.

Battery

The battery according to a preferred embodiment is a battery pack consisting of six 1400 mAh LiPo (Lithium Polymer) battery cells. The updated version of this battery pack does not have connectors between the cells. Instead, the cells are directly wired together. The characteristics of this battery are set out as follows: Voltage: 11.1V; Maximum Current Draw: 3.5 A; Maximum Power Output: 38.85 W; and Battery Life: 1 hour on maximum temperature setting. Preferably, it is a rechargeable battery which can be recharged by plugging with the appropriate outlet into a standard electrical socket. Table 3 provides for some of the characteristics of the battery used according to a preferred embodiment.

TABLE 3

Characteristics of the Battery

| | |
|---|---|
| Total Voltage | 11.1 v |
| Total Capacity | 2800 mAh |
| Nominal Current Drain | 3 A-4 A |
| Configuration | 3S1P or 3S2P |
| Available space | 24-25 cm × 2.8-3.3 cm × 1.0 cm Thickness of cell should not exceed 1.0 cm |
| Protection | 4 A continuous operation (9-12 A disconnect) Over Heat (65° C.) |
| Battery connection | 1.4 mm barrel (female), 22AWG silicone wiring |

Preferably, the battery packaging is designed to allow flexibility as follows: it is bendable longitudinally (horizontally) with three rigid segmented areas of under 6-7 cm each; and the battery connection terminates at location specified on assembled battery pack.

The battery charger according to a preferred embodiment is a 12.6V IA charger for the previously mentioned battery pack. It is certified by the following safety standards: Safety standard: UL1310 & EN55014; and EMC standard: FCC CE(EN55024,EN6100) C-TICK.

Temperature Controller

The temperature controller, in the preferred embodiment illustrated, is a button used to control the heat settings as well as power ON and OFF the heating pads. It is composed of a silicone covering with a printed circuit board (PCB) embedded within it. The following provides the specification thereof: Input voltage: 5v~18v and work current from 0 A~4 A.

Figure 5:
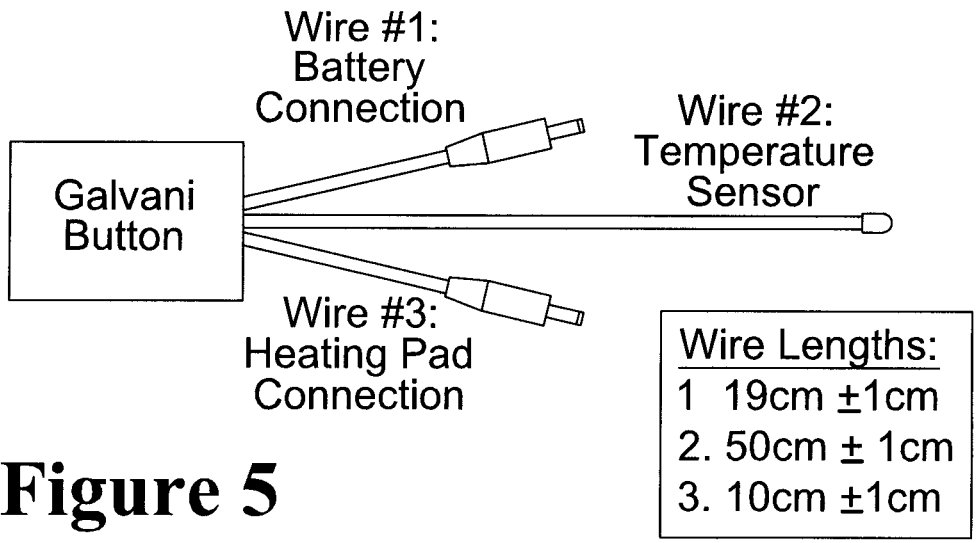
FIG. 5 is a schematic view of the electrical connections of the hand warmer according to a preferred embodiment of the present invention.
Figure 6:
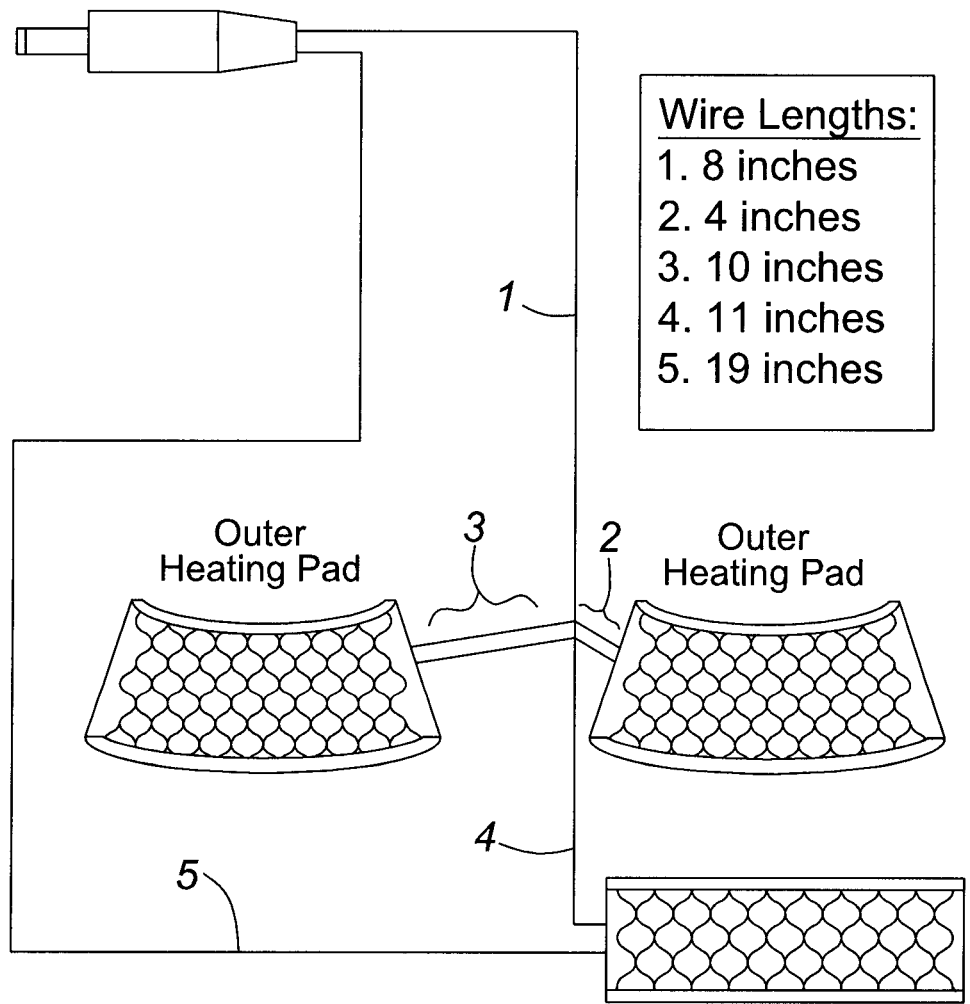
FIG. 6 is a schematic view of the electrical connections between the connector and the various heating elements of the hand warmer according to a preferred embodiment of the present invention.

According to a preferred embodiment, the heat settings provide turn off temperature at 115° C. (when heat setting is at Max); 105° C. (when heat setting is at High); 95° C. (when heat setting is at Medium); and 85° C. (when heat setting is at Low). FIG. 5 shows the device preferably comprising a temperature sensor connected to the printed circuit board which allows monitoring of the temperature inside the hand warmer and in the event that the temperature exceeds any of the various settings (Max, High, Medium and Low) the heaters will be turned off by the device. FIG. 6 shows the heating pads connections between one another and with the male barrel connector adapted to be inserted into the female barrel end of wire #3 (see FIG. 5).

According to a preferred embodiment, the two openings of the sleeve have a tubular cuff preferably made of fabric that is substantially self-closing and which cuffs are adapted to comfortably allow a user's hand to penetrate the longitudinal opening inside the sleeve of the hand warmer.

Figure 7:
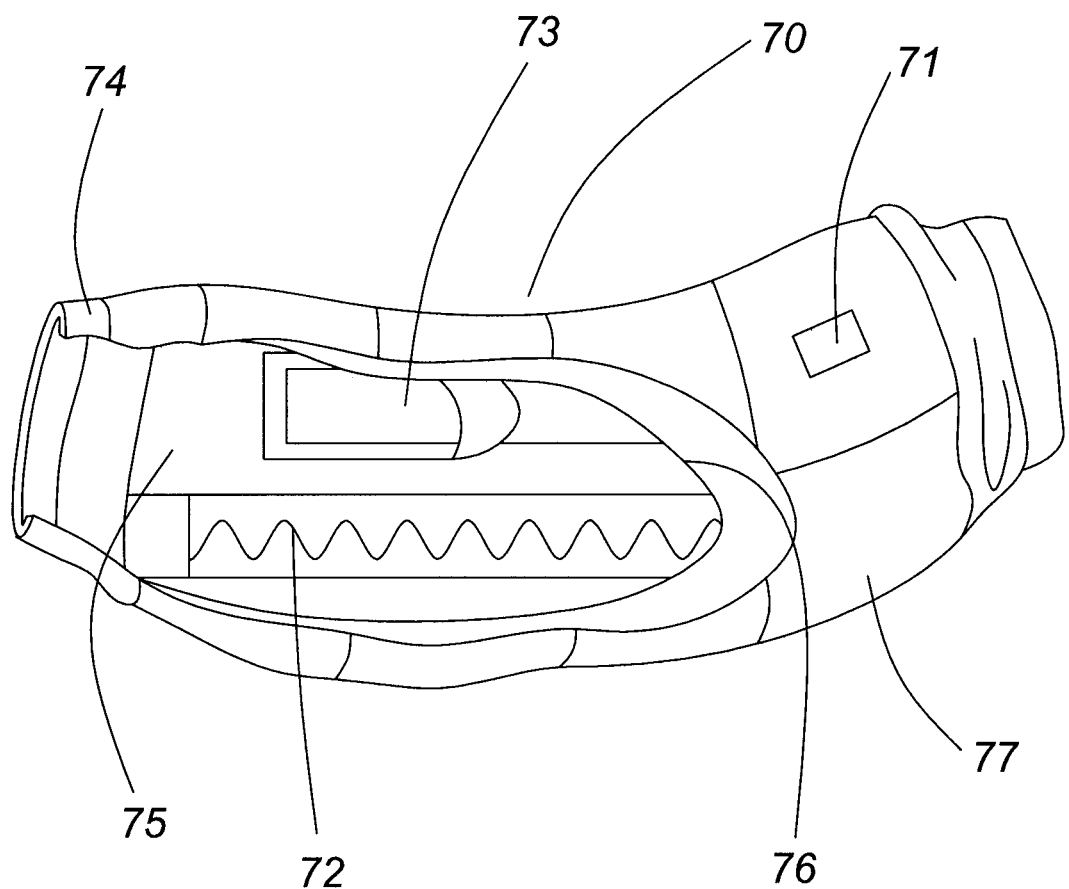
FIG. 7 is a exposed front view of a preferred embodiment.

FIG. 7 illustrates a preferred embodiment of the present invention. The exterior shell (77) of the handwarmer (70) is made of hydrophobic fabric which is weather resistant, moisture-wicking fabric technology keeps sweat and odor out and keeps dry heat in. It also comprises a tri-zone heating system with heated surfaces in the front (76), back (75) and in the grab bar (72) surround cold hands for efficient heat transfer. The heating surfaces are powered with lithium polymer batteries (73) which are rechargeable batteries and can provide up to five (5) hours of sustained use in the most extreme conditions. The handwarmer (70) also incorporates a seal on the cuffs (74) which allows to maintain the handwarmer sealed when not in use simply by pressing the opposite edges of the cuffs together. The variable heat adjustment system (71) allows the user to easily change between four (4) heat levels by simply pressing a button.

Figure 8:
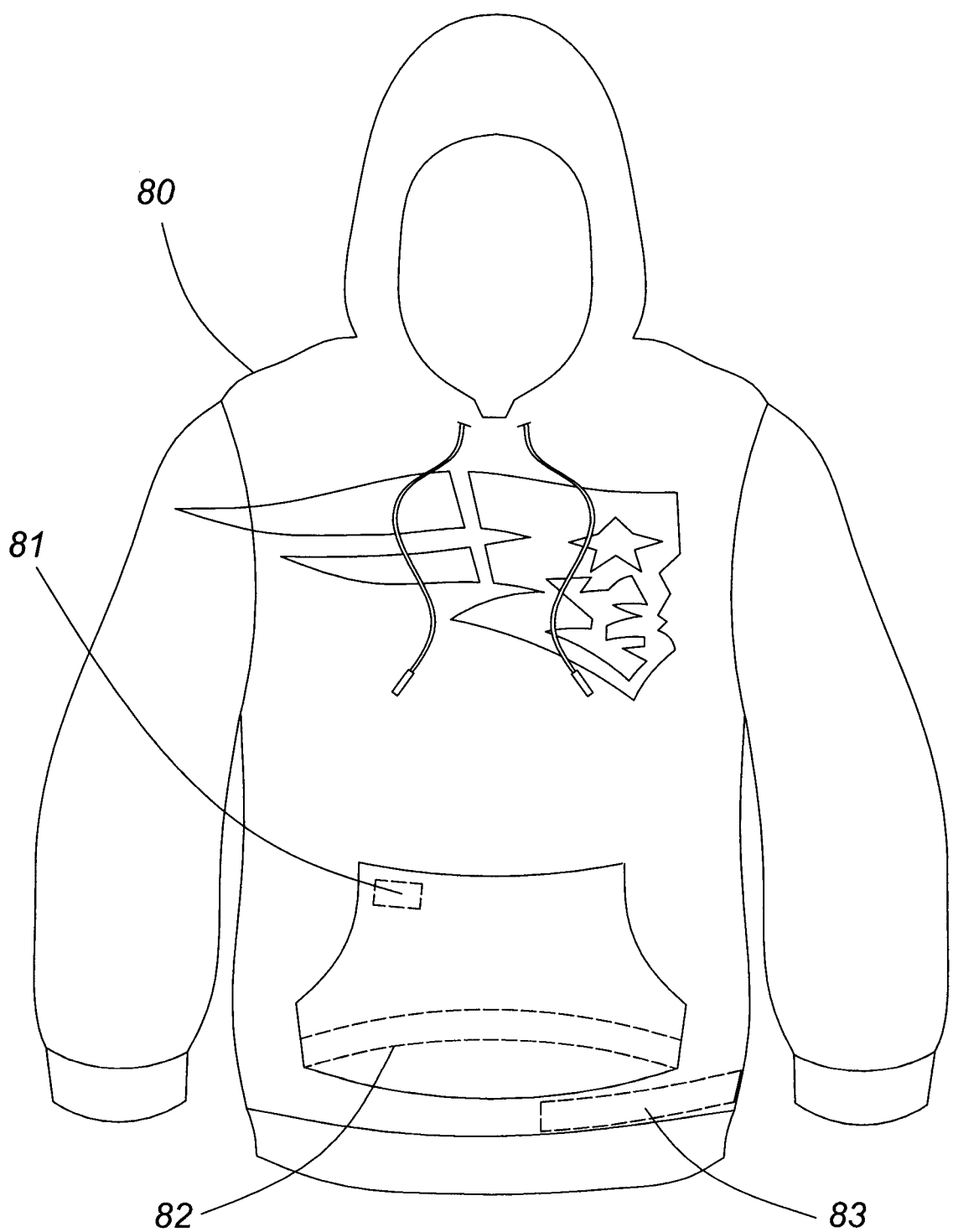
FIG. 8 is a front view of a hoodie comprising a preferred embodiment of the invention.

FIG. 8 illustrates another embodiment of the present invention where the heated grab bar (82) is incorporated into a hoodie (80) and where the hoodie is adapted to contain a battery pack (83) and and variable heat adjustment system (81).

While the invention has been described in detail with reference to preferred embodiments thereof, it is apparent that those skilled in the art, upon learning of the invention, will visualize yet other embodiments that are within the scope of the invention, Thus it is intended that the scope of the invention be limited only by the following claims.

What is claimed is:

1. A hand warmer comprising:
    a tubular sleeve having two extremities located along a longitudinal axis thereof, said sleeve defining a longitudinal opening therein, each extremity defining an opening adapted to receive hands;

wherein said tubular sleeve comprises an inner wall and an outer wall; a flexible handlebar-shaped heating element that comprises a heating wire that is encased in a thin, flexible heating pad, the flexible handlebar-shaped heating element adapted to be grasped by a hand or hands when inserted into the longitudinal opening, the flexible handlebar-shaped heating element is secured to the inner wall of the tubular sleeve at both ends of the handlebar-shaped heating element, wherein the flexible handlebar-shaped heating element is formed from the thin, flexible heating pad, the heating wire of the thin, flexible heating pad connected to a battery, and wherein the entire flexible handlebar-shaped heating element is flexible.

2. The hand warmer according to claim 1, wherein the thickness of the thin, flexible heating pad does not exceed 2 mm.

3. The hand warmer according to claim 2, wherein the flexible handlebar-shaped heating element is parallel or perpendicular to the longitudinal opening of the tubular sleeve.

4. The hand warmer according to claim 3, wherein the hand warmer further comprises a self-closing fabric located around the opening in a back portion of the tubular sleeve where hands are to be inserted.

5. A hand warmer comprising:
a tubular sleeve comprising an inner wall and outer wall, and a front portion and a back portion, the tubular sleeve having at least two open ends adapted to receive hands, said sleeve defining a longitudinal opening;
a battery operatively connected to a flexible handlebar-shaped heating element adapted to receive hands that comprises a heating wire, the first heating wire encased within a first thin, flexible heating pad, the flexible handlebar-shaped heating element located within the longitudinal opening, the flexible handlebar-shaped heating element secured at least at one or more points of the tubular sleeve, wherein the flexible handlebar-shaped heating element is formed from the thin, flexible heating pad, the thin, flexible heating pad securing the heating wire connected to the battery; a self-closing fabric located around each opening of the tubular sleeve; and
heat capture fabric located within a space defined by the inner wall and the outer wall of the sleeve, wherein the flexible handlebar-shaped heating element is flexible in its entirety.

6. The hand warmer according to claim 5, wherein the thickness of the thin, flexible heating pad is no greater than 2 mm.

7. A hand warmer comprising:
a tubular sleeve having two extremities located along a longitudinal axis thereof, said sleeve defining a longitudinal opening therein, each extremity defining an opening adapted to receive hands, the tubular sleeve having a front portion and a back portion;
at least one heating element; and a battery operatively connected to the at least one heating element;
wherein said tubular sleeve comprises an inner wall and an outer wall and is adapted to receive the battery between the inner and outer wall and wherein the at least one heating element is flexible, handlebar-shaped, and adapted to be grasped by a hand or hands when inserted into the longitudinal opening, the at least one heating element comprises a heating wire, the heating wire encased in a thin, flexible heating pad,
wherein the entire at least one heating element is as flexible.

8. A hand warmer comprising:
a tubular sleeve defining a longitudinal opening formed between each extremity of a longitudinal axis of the tubular sleeve, wherein the tubular sleeve has an inner wall and an outer wall and each of the extremities defines an opening adapted to receive hands and provide access to the longitudinal opening;
a flexible handlebar-shaped heating element secured to the inner wall of the tubular sleeve and formed from a thin, flexible heating pad encasing a heating wire, wherein the thin, flexible heating pad does not exceed 2 mm in thickness; and
a battery operably connected to the flexible handle-bar shaped heating element, wherein the battery is retained between the inner wall and the outer wall of the tubular sleeve;
wherein the entire flexible handlebar-shaped heating element is flexible; and
wherein the tubular sleeve has a downward arcuate shape.

9. The hand warmer according to claim 7, wherein the thin, flexible heating pad has a thickness of 2 mm or less.

* * * * *